United States Patent [19]
de Radzitzky d'Ostrowick et al.

[11] 3,935,289

[45] Jan. 27, 1976

[54] SELECTIVE HALOGENATION OF PARAFFINS

[76] Inventors: Pierre M. J. G. de Radzitzky d'Ostrowick, 101 Avenue Paul Hymans - Woluwe-St-Lambert; Jacques D. V. Hanotier, 36 Avenue Docteur Decroly - uccle., 18 Brussels; Joseph M. E. Vaerman, 28, Clos Fernand Tonnet, 9 Jette - Brussels, all of Belgium

[22] Filed: Dec. 11, 1969

[21] Appl. No.: 884,317

[30] Foreign Application Priority Data
Apr. 11, 1969 Belgium .................................. 69601

[52] U.S. Cl. ............................... 260/660; 260/659 R
[51] Int. Cl.² ........................................ C07C 109/04

[58] Field of Search ........ 260/659 R, 658 R, 654 R, 260/660

[56] References Cited
UNITED STATES PATENTS

| | | | |
|---|---|---|---|
| 2,548,764 | 3/1951 | Ayers et al. | 260/659 |
| 2,831,036 | 3/1958 | Wiese | 260/659 |
| 2,914,572 | 11/1959 | Amir | 260/659 |

Primary Examiner—James O. Thomas, Jr.
Assistant Examiner—A. Siegel

[57] ABSTRACT

Paraffins are selectively chlorinated or brominated in position alpha to a terminal methyl group by reacting with a halogen donor in the presence of a cobaltic salt and an acid activator in an inert atmosphere.

12 Claims, No Drawings

SELECTIVE HALOGENATION OF PARAFFINS

The present invention relates to a process for selective halogenation of paraffins by reaction of the paraffin with a halogen donor in the presence of a cobaltic salt and a strong acid activator and in the absence of molecular oxygen.

The chlorination of hydrocarbons in vapor or liquid phase by such halogenating agents as molecular chlorine or sulphuryl chloride has been the subject of a considerable amount of work. It was found in all cases that the replacement of an atom of hydrogen by an atom of chlorine occurs with increasing ease in the order primary<secondary<tertiary, and this in a manner which is more pronounced the lower the temperature. In the case of a straight-chain paraffin, this reactivity rule results in the fact that the terminal methyl groups possess a higher resistance to chlorination than the internal methylene groups and these are attacked in statistical manner (P. Asinger, *Chemie u. Technologie der Paraffin-Kohlenwasserstoffe*, Akademie-Verlag, Berlin, 1956, p. 567). Analogously, in the case of a branched-chain paraffin, the tertiary C—H bonds are chlorinated more easily than the secondary bonds of the methylene groups. These rules equally prevail for other halogenations such as bromination. For example, it has been demonstrated that during the bromination of isopentane, the teritary C—H linkage reacts from thirty to forty times more rapidly than secondary C—H methylene bonds of the same molecule (C. A. Russel and H. C. Brown, *J. Amer. Chem. Soc.*, Vol. 77, p. 4025, 1955).

We have now discovered, however, that it is possible to carry out a selective attack on a secondary C—H bond situated at the alpha position to a terminal methyl group, even despite the presence of tertiary hydrogen atoms within the same molecule.

It is the main object of the present invention to provide a process for selective halogenation comprising bromination or chlorination of straight-chain or branched-chain paraffins; and, more specifically, to provide a process in which such halogenation occurs on a methylene group adjacent to a terminal methyl group. Another object of the invention is to provide a process in which this halogenation is carried out at low temperature.

According to the present invention a process is provided for halogenation of paraffins, straight-chain or branched-chain, by reaction of the paraffin with a halogen donor in the liquid phase in the presence of a cobaltic salt and an activator consisting of an acid whose dissociation constant exceed $5 \times 10^{-3}$, or of boron trifluoride or a mixture of these. The halogen donor is a compound having at least one atom of chlorine or bromine linked to a radical which is inert to the paraffin under the conditions of the reaction. The reaction is carried out in the absence of molecular oxygen, and at a temperature between −20°C and +100°C.

The present halogenation process may be applied to any straight-chain or branched-chain paraffin of the $CH_3$—$CH_2$—R type, in which R is any primary alkyl radical, irrespective of its structure. However, the characteristic selectivity of the process is particularly pronounced if the paraffin comprises at least two methylene groups, of which one but not both are adjacent to a terminal methyl group. This category of paraffins may be represented by the follwoing structural formula:

$$CH_3—CH_2—CH_2—R'$$

wherein R' is any alkyl higher than methyl. For example, R' may be an ethyl group to define n-pentane by this formula, which is converted selectively into 2-halopentane by the present halogenation process. R' may equally be a secondary alkyl radical. For example, R' may be the isopropyl group whereby the formula will define 2-methylpentane which by this halogenation becomes converted into 2-methyl-4-halopentane. This second example will demonstrate the unexpected selectivity of this process, since such paraffin having a tertiary C—H bond would have been attacked preferentially by other known halogenation methods to yield a substantial proportion of 2-methyl-2-halopentane. R' may also be a tertiary radical, for example, the t-butyl group; and here again, the methylene group adjacent to the terminal methyl will be preferentially halogenated. The examples above are given by way of illustration, only to provide a clearer understanding of the unique selectivity of this process, which, as shown by the examples below, is confirmed for all paraffins corresponding to the preceding formula, irrespective of the structure of the alkyl radical R'. Hence, any paraffin of whatever chain length, even solids including high molecular weight paraffin waxes, may be halogenated. Generally the paraffins hereof will have less than sixty carbon atoms such as between five and sixty carbon atoms.

It is not necessary but often useful to employ a solvent for effecting this halogenation process in the liquid phase. In many cases, merely mixing the reactants results in a homogeneous solution in which the halogenation reaction may occur. In other cases, however, the reactants will preferably be dissolved in a solvent. As a general rule, any liquid may be employed which is substantially inert under the conditions of the reaction and in which the paraffin as well as the other reactants, are soluble. The lower fatty acids having from 2 to 4 carbon atoms and the lower esters, particularly the methyl and t-butyl esters, of said fatty acids fulfill the preceding conditions satisfactorily and are preferred. Acetic acid is a particularly advantageous solvent.

To halogenate a paraffin according to the process of the invention, it is essential for the listed reactants specified above — cobaltic salt, halogen donor and acid activator — to be used together and at the same time. No appreciable halogenation occurs if one of these reactants is omitted from the system. The mechanism of the reaction and the part played by each of these reactants are not known with certainty. However, a possible mechanism may usefully be visualized according to the following scheme where the paraffin, the acid activator, the cobaltic salt and an active species derived therefrom are represented respectively by RH, AH, $Co^{3+}$ and Co(III):

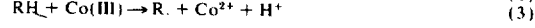

$$AH \rightleftharpoons A^- + H^+ \qquad (1)$$
$$Co^{3+} + H^+ \rightarrow Co(III) \qquad (2)$$
$$RH + Co(III) \rightarrow R\cdot + Co^{2+} + H^+ \qquad (3)$$

In the presence of a halogen donor BX in which X represents an atom of chlorine or bromine, the following reaction would then occur:

$$R\cdot + BX \rightarrow RX + B\cdot \qquad (4)$$

By contrast, in the absence of a halogen donor, the radical R. would be oxidized in its turn while yielding a carbonium salt, which in the presence of a carboxylic solvent would result in an ester as disclosed in co-pending application Ser. No. 884,336 (LAB 053) filed Dec.

11, 1969, and now U.S. Pat. No. 3,665,030, patented May 23, 1972 and Belgian Pat. No. 719,094:

$$R. + Co(III) \rightarrow R^+ + Co^{2+} \quad (5)$$
$$R^+ + R'COOH \rightarrow ROCOR' \quad (6)$$

The radical nature of the product of the primary attack of the paraffin (reaction nr. 3) is in no doubt, since in the present process as in the conventional halogenation processes, the reaction is very highly inhibited by oxygen, which cannot be explained except by the reaction:

$$R. + O_2 \rightarrow ROO. \quad (7)$$

The nature of the cobaltic salt employed in the invention may vary within wide limits. However, the cobaltic salts of the carboxylic acids have the advantage of being easily soluble as a rule in an organic medium and of being easily produced from the corresponding cobalt (II) salts. The cobaltic salts of the lower fatty acids, that is to say, comprising from 2 to 4 carbon atoms, and more specifically still, cobaltic acetate, are particularly advantageous in this respect. Cobaltic acetate may be produced, for example, by co-oxidation of cobalt (II) acetate with acetaldehyde in acetic acid in the presence of oxygen as described in U.S. Pat. No. 1,976,757. The cobaltic salts of the other fatty acids may be produced in analogous manner or by exchange reaction between these and cobaltic acetate.

As stated in the foregoing, however, these cobaltic salts do not react in sufficient rate with the paraffins unless they are activated by a relatively strong inorganic or organic acid. The most appropriate acids for this function are those whose dissociation constant K exceeds $5 \times 10^{-3}$. They should be soluble in the reaction medium, and should not interfere with the reaction. Useful examples are sulphuric acid ($K_1 > 1$), perchloric acid ($K > 1$), trifluoroacetic acid ($K = 6 \times 10^{-1}$), trichloroacetic acid ($K = 2 \times 10^{-1}$), tribromoacetic acid ($K = 2 \times 10^{-1}$), dichloroacetic acid ($K = 3.3 \times 10^{-2}$), phosphoric acid ($K_1 = 7.5 \times 10,^{-3}$), and the like. Some Lewis acids like boron trifluoride also have an activating action. A mixture of these acids may also be employed. However, acids containing chlorine, bromine or iodine in ionic form, such as hydrochloric acid, hydrobromic or hydroiodic acid, or else aluminium trichloride, are generally avoided since they can interfere with the reaction. Hydrochloric acid, for example, effects a substantial chlorination in a non-selective manner, very probably resulting from an attack on the paraffin by chlorine radicals coming from the reaction:

$$Cl^- + Co^{3+} \quad Cl + Co^{2+} \,{}^{(8)}$$

The acids specified have a promoting action on both the rate and the progress of the reaction. This effect is more pronounced the stronger the acid and, up to some limit, the higher its concentration. On the other hand, the quantity of acid should be correlated to the quantity of cobaltic salt employed. For example, if sulphuric acid is employed as an activator, a molar ratio between the acid and salt of approximately 2 is necessary to obtain a maximum of activity. With a weaker acid like trifluoroacetic acid, a ratio of between five and twenty is preferable. These different facts, as well as the great variety of acids able to perform the function of an activator suggest that their action depends less on the nature of their anion than on their ability to release protons, according to reactions 1 and 2 postulated above.

The halogen donor is a member of the group consisting of molecular bromine and a compound having the formula

where X is a chloro or bromo radical; $Y_1$ and $Y_2$ are members of the group consisting of the fluoro, chloro, cyano, carboxyl, alkoxycarbonyl, acyl, hydrogen and hydrocarbon radicals; $Y_3$ is a fluoro, chloro, bromo, cyano, carboxyl, alkoxycarbonyl or acyl radical. Specific conditions are fulfilled by these halogen donors. By considering the reaction scheme suggested above, for high yield of halogenated products the reaction (4) should predominate compared to the reaction (5) which results in forming oxygenated products. Accordingly, the activation energy of the reaction (4) should be small, and to this end, the dissociation energy of the B-X bond should be distinctly lower than that of the R-X bond. On the other hand, to maintain the selectivity of the process, the radical B. released by the reaction (4) should be inert relative to the substrate i.e. the following reaction does not take place:

$$RH + B. \rightarrow R. + BH \quad (9)$$

To this end, the dissociation energy of the B—H bond should be distinctly lower than that of the R—H bond. These two conditions are fulfilled if the radical B. is highly stabilized by resonance. This applies in the case of the radicals of the types $.CX_3$, $.CHX_2$, $.CH_2X$ in which X represents an atom of fluorine, chlorine or bromine. It equally applies in the case of radicals of the types $.CX_2COOH$, $.CHXCOOH$, $.CX_2COOR$, $.CX_2CN$, which are stabilized by conjugation with carbonyl or cyano groups.

Accordingly, halogenated compounds useful as halogen donors are the halomethanes comprising at least two halogen atoms selected from the group consisting of fluorine, chlorine and bromine. Examples of this category of compounds are carbon tetrachloride, trichlorobromomethane, dichlorodibromomethane, chlorotribromomethane, carbon tetrabromide, difluorodibromomethane, bromoform, chlorodibromomethane, dichlorobromomethane, chloroform and methylene chloride. Equally useful as halogen donors are the compounds comprising at least one atom of bromine or two atoms of chlorine linked to one and the same carbon atom situated in the alpha position of a carbonyl or cyano group. Examples of this category of compounds are trichloroacetic acid, dichloroacetic acid, tribromoacetic acid, dibromoacetic acid, bromoacetic acid, alpha-bromoisobutyric acid, the esters of such acids, trichloroacetonitrile and dibromoacetonitrile. It will be noted that this list includes some acids which can be halogen donors and which also have a dissociation constant equally enabling these to act as an activator. In particular, this applies in the case of trichloroacetic acid and tribromoacetic acid. Acids of this kind may effectively perform both functions in one and the same reaction.

Molecular bromine may also be used as a halogen donor since it fulfills the two energy conditions specified above; that is, its dissociation energy (46 Kcal) is distinctly lower than that of the R—X bond of an alkyl bromide (59 to 67 Kcal) and, on the other hand, the dissociation energy of the H-Br bond (87 Kcal) is lower than that of the C—H bond of a paraffin (90 to 102 Kcal). This is not so in the case of molecular chlorine the use of which results in non-selective chlorination.

For the yield of halogenated products of the process to be high, it is necessary not only to employ an effective halogen donor, but also to use it in sufficient quantity. If the attack on the paraffin is performed according to the reaction (3), the halogen donor should be present in a quantity at least equivalent, on a molar basis, to the quantity of cobaltic salt, in order that the radicals coming from this attack may react usefully. It would even be preferable to have an excess of halogen donor above this quantity for optimum promotion of the halogenation reaction. In practice, a concentration of halogen donor from 1.5 to 15 times greater than that of the cobaltic salt is sufficient as a rule to secure good results. In particular cases, however, it may be advantageous to employ even greater quantities; and contingently even to employ the halogen donor as a solvent.

The quantity of cobaltic salt to be employed evidently depends on the degree of conversion desired. The halogenation of a paraffin molecule by the process of the invention requires the reduction of 2 to 10 atoms of cobalt, according to conditions. However, it is advantageous as a rule to limit conversion in such manner as to prevent secondary reactions.

Beyond the factors specified above, it should also be noted that to secure a high yield of halogenated products, it is of importance for the reaction mixture to be as free of water as possible. The presence of water promotes the formation of oxygenated products, specifically of ketones, at the expense of the halogenated products. Finally, it should be recalled that the same action occurs in drastic manner in the presence of molecular oxygen and the reaction should be carried out in an inert atmosphere free from oxygen.

The invention will be further described with reference to the following examples:

EXAMPLE I

This example illustrates the chlorination of n-heptane by means of the system comprising cobaltic acetate, sulphuric acid, and carbon tetrachloride.

A solution containing 0.5 mol/liter of n-heptane, 0.1 mol/liter of cobaltic acetate, 0.2 mol/liter of sulphuric acid and 1.5 mol/liter of carbon tetrachloride in acetic acid, was kept at 20°C, without stirring, under an atmosphere of pure nitrogen at atmospheric pressure. After 90 minutes, the reaction mixture was diluted with a saturated solution of sodium chloride in water and subjected to repeated extractions with ether. Analysis by vapor phase chromatography of the ether extract enabled to identify the following productd whose relative proportions are expressed as molar percentages:

heptyl chlorides:69% (isomer 1: 6%; 2: 65%; 3: 19%; 4:10%)
heptyl Acetates:16% (isomer 1: 0%; 2: 70%; 3: 22%; 4: 8%)
heptanoes:8% (isomer 1: 0%; 2: 70%; 3: 24%; 4: 6%)
heptanone:7% isomer 2: 73%; 3: 19%; 4: 8%)

No product of any kind was detected when omitting either sulphuric acid or cobaltic acetate in the reaction medium.

This example demonstrates the need to employ a cobaltic salt and an acid activator to obtain halogenated products by the present process.

EXAMPLE II

This example illustrates the chlorination of n-heptane by means of the system comprising cobaltic acetate, sulphuric acid and trichloroacetic acid.

By operating as in Example I but replacing carbon tetrachloride with trichloroacetic acid in the same concentration, the following products were identified whose relative proportions are expressed as molar percentages:

heptyl chlorides:55% (isomer 1: 9%; 2: 62%; 3: 21%; 4: 8%)
heptyl acetates:23% (isomer 1: 0%; 2: 70%; 3: 20%; 4: 10%)
heptanols:17% (isomer 1: 0%; 2: 55%; 3: 24%; 4: 21%)
heptanones:5% (isomer 2: 80%; 3: 12%; 4: 8%)

EXAMPLE III

This example illustrates the chlorination of n-heptane by means of the system comprising cobaltic acetate, sulphuric acid and chloroform.

By operating as in Example I, but replacing carbon tetrachloride with chloroform in the same concentration, the following products were identified whose relative proportions are expressed as molar percentages:

heptyl chlorides:64% (isomer 1: 7%; 2: 50%; 3: 32%; 4: 11%)
heptyl acetates:13% (isomer 1: 0%; 2: 69%; 3: 23%; 4: 8%)
heptanols:14% (isomer 1: 0%; 2: 59%; 3: 33%; 4: 8%)
heptanones:9% (isomer 2: 56%; 3: 29%; 4: 15%)

EXAMPLE IV

This example illustrates the chlorination of n-heptane by means of the system comprising cobaltic acetate, sulphuric acid, and methylene chloride.

By operating as in Example I, but replacing carbon tetrachloride with methylene chloride in the same concentration, the following products were identified whose proportions are expressed as molar percentages:

heptyl chlorides:63% (isomer 1: 5%; 2: 57%; 3: 27%; 4: 11%)
heptyl acetates:17% (isomer 1: 0%; 2: 68%; 3: 23%; 4: 9%)
heptanols:13% (isomer 1: 0%; 2: 64%; 3: 29%; 4: 7%)
heptanones:7% (isomer 2: 64%; 3: 26%; 4: 10%)

EXAMPLE V

This example illustrates the chlorination of n-heptane by means of the system comprising cobaltic acetate, perchloric acid, and carbon tetrachloride.

A solution containing 0.5 mol/liter of n-heptane, 0.1 mol/liter of cobaltic acetate, 1.0 mol/liter of perchloric acid, and 1.5 mol/liter of carbon tetrachloride in acetic acid was kept at 20°C, without stirring, under a nitrogen atmosphere at atmospheric pressure. After 18 hours, the reaction mixture was treated as in Example I. The analysis of the ether extract enabled to identify the following products, whose relative proportions are expressed as molar percentages:

heptyl chlorides:65% (isomer 1: 6%; 2: 59%; 3: 23%; 4: 12%)

heptyl acetates:29% (isomer 1: 0%; 2: 66%; 3: 24%; 4: 10%)

heptanols:5% (isomer 1: 0%; 2: 57%; 3: 30%; 4: 13%)

heptanones:1% (isomer 2: 49%; 3: 30%; 4: 21%)

EXAMPLE VI

This example illustrates the chlorination of n-heptane by means of the system comprising cobaltic acetate, boron trifluoride, and carbon tetrachloride.

By proceeding as in Example V, but replacing perchloric acid with boron trifluoride at a concentration of 1.5 mol/liter, chromatographic analysis enabled to identify the following products whose relative proportions are expressed as molar percentages:

heptyl chlorides:50% isomer 1: 1%; 2: 54%; 3: 33%; 4: 12%)

heptyl acetates:28% (isomer 1: 0%; 2: 65%; 3: 30%; 4: 5%)

heptanones:14% (isomer 2: 62%; 3: 26%; 4:12%)

heptanols:8% (isomer 2: ± 100%)

EXAMPLE VII

This example illustrates the chlorination of n-heptane by means of the system comprising cobaltic acetate, trifluoroacetic acid and carbon tetrachloride.

By proceeding as in Example V but replacing perchloric acid with trifluoroacetic acid at the concentration of 1.5 mol/liter, analysis showed that 4.3% of the n-heptane employed had been converted to yield the following products whose relative proportions are expressed as molar percentages:

heptyl chlorides:92% (isomer 1: 4%; 2: 80%; 3: 10%; 4: 6%)

heptyl acetates:4% (isomer 1: 0%; 2: 80%; 3: 15%; 4: 5%)

heptanols:3% (isomer 1: 0%; 2: 77%; 3: 23%; 4: 0%)

heptanones:1% (isomer 2: 82%; 3: 18%; 4: 0%)

It is apparent that by employing trifluoroacetic acid as an activator, the heptane is converted almost exclusively into heptyl chlorides with a particularyly high selectivity in respect of isomer 2.

EXAMPLE VIII

This example illustrates the chlorination of n-heptane by means of the system comprising cobaltic acetate, trichloroacetic acid, and carbon tetrachloride.

Applying the procedure of Example V, but replacing perchloric acid with trichloroacetic acid at the concentration of 1.5 mol/liter, analysis showed that 3.2% of the n-heptane employed had been converted to yield the following products whose relative proportions are given as molar percentages.

heptyl chlorides:89% (isomer 1: 7%; 2: 73%; 3: 13%; 4: 7%)

heptyl acetates:5% (isomer 1: 0%; 2: 77%; 3: 16%; 4: 7%)

heptanols:5% isomer 1: 0%; 2: 80%; 3: 16%; 4: 4%)

heptanones:1% (isomer 2: 72%; 3: 19%; 4: 9%).

EXAMPLE IX

This example illustrates the chlorination of n-heptane by means of the system comprising cobaltic acetate and trichloroacetic acid.

A solution containing 0.5 mol/liter of n-heptane, 0.1 mol/liter of cobaltic acetate, and 1.5 mol/liter of trichloroacetic acid in acetic acid was kept at 20°C, without stirring, under a nitrogen atmopshere at atmospheric pressure. After 18 hours the reaction mixture was treated and analyzed as in Example I. It was thus established that 3.3% of the n-heptane employed had been converted to yield the following products whose relative proportions are given as molar percentages heptyl chlorides:60% (isomer 1: 6%; 2: 79%; 3: 12%; 4: 5%)

heptyl acetates:13% (isomer 1: 6%; 2: 74%; 3: 14%; 4: 6%)

heptanols:9% (isomer 1: 0%; 2: 81%; 3: 15%; 4: 4%)

This example shows that trichloroacetic acid can simultaneously operate as an activator and as a halogen donor.

EXAMPLE X

By operating in the same conditions as in Example IX, but taking special precautions to obtain as anhydrous a medium as possible, it was established that 2.8 % of the n-heptane had been converted to yield the following products whose relative proportions are given as molar percentages:

heptyl chlorides: 80% (isomer 1: 7%; 2: 79%; 3: 9%; 4: 5%)

heptyl acetates: 14% (isomer 1: 0%; 2: 78%; 3: 16%; 4: 6%)

heptanols: 5% (isomer 1: 0%; 2: 74%; 3: 13%; 4: 13%)

heptanones: 1% (isomer 2: 93%; 3: 7%; 4: 0%)

Comparing these results to those of Example IX, it is plain that the proportion of halides is distinctly improved by operating in an anhydrous medium.

EXAMPLE XI

This example illustrates the chlorination of n-heptane by means of the system comprising cobaltic acetate and trichloroacetic acid, using propionic acid as a solvent.

A solution containing 0.5 mol/liter of n-heptane, 0.2 mol/liter of cobaltic acetate, and 1.5 mol/liter of trichloroacetic in propionic acid was kept at 25° C, without stirring, under a nitrogen atmosphere at atmospheric pressure. After 18 hours the reaction mixture was treated as in Example I. Analysis showed that approximately 80% of the products obtained consisted of heptyl chlorides (isomer 1: 6%; 2 : 80%; 3 : 10%; 4 : 4%).

Operating in the same conditions but replacing cobaltic acetate with cobaltic propionate, identical results were obtained.

EXAMPLE XII

This example illustrates the chlorination of n-heptane by means of the system comprising cobaltic acetate and trichloroacetic acid, using methyl acetate as a solvent.

Example XI was repeated, replacing propionic acid with methyl acetate. Analysis enabled to identify the following products whose relative proportions are given as molar percentages:

heptyl chlorides:72% (isomer 1: 10%; 2 : 76%; 3: 10%; 4: 4%)
heptyl acetates:16% (isomer 1: 13%; 2 : 67%; 3: 15%; 4: 5%)
heptanols:7% (only isomer 2 was detectable)
heptanones:5% (only isomer 2 was detectable)

EXAMPLE XIII

This example illustrates the chlorination of n-heptane by means of the system comprising cobaltic acetate and trichloroacetic acid in the absence of extraneous solvent.

A solution containing 0.1 mol/liter of cobaltic acetate and 0.75 mol/liter of trichloroacetic acid in n-heptane was kept at 20°C, without stirring, under a nitrogen atmosphere at atmospheric pressure. After 18 hours the reaction mixture was treated and analyzed as in Example I. Analysis enabled to identify the following products, whose relative proportions are given as molar percentages:

heptyl chlorides:57% (isomer 1; 16%; 2: 68%; 3: 12%; 4: 4%)
heptanols:27% (isomer 1: 0%; 2: 78%; 3: 18%; 4: 4%)
heptanones:11% (isomer     2: 86%; 3: 11%; 4: 3%)
heptyl acetates:5% (isomer 1: 0%; 2: 70%; 3: 21%; 4: 9%)

EXAMPLE XIV

This example illustrates the chlorination of n-heptane by means of the system comprising cobaltic acetate, trichloroacetic acid, and carbon tetrachloride, in the absence of extraneous solvent.

A solution containing 0.5 mol/liter of n-heptane, 0.1 mol/liter of cobaltic acetate and 1.5 mol/liter of trichloroacetic acid in carbon tetrachloride was kept at 20°C, without stirring, under a nitrogen atmosphere at atmospheric pressure. After 18 hours the reaction mixture was treated and analyzed as in Example I. Analysis enabled to identify the following products, whose relative proportions are given as molar percentages:

heptyl chloride:75% (isomer 1: 15%; 2: 68%; 3:12%; 4: 5%)
heptanols:25% (isomer 1: 0%; 2: 71%; 3:23%; 4: 6%)

This example illustrates the possibility of using the halogen donor as a solvent.

EXAMPLE XV

This example illustrates the effect of temperature on the chlorination of n-heptane by means of the system comprising cobaltic acetate, and trichloroacetic acid.

Example IX was repeated at different temperatures. In all cases the major proportion of the products obtained consisted of heptyl chlorides whereof the isomeric distribution is given in the following table, equally repeating the results of Example IX.

| Temperatures (°C) | Heptyl chlorides (% relative) | | | |
|---|---|---|---|---|
| | 1 | 2 | 3 | 4 |
| 20 | 6 | 77 | 12 | 5 |
| 35 | 8 | 79 | 8 | 5 |
| 70 | 9 | 64 | 20 | 7 |
| 90 | 9 | 55 | 27 | 9 |

These results show that the selectivity for isomer 2 is practically identical at 20° and at 35°C, but that it decreases at higher temperatures to approach the statistical value (40 percent while ignoring the contribution of the methyl groups).

EXAMPLE XVI

This example illustrates the bromination of n-heptane by means of the system comprising cobaltic acetate, sulphuric acid, and trichlorobromomethane.

A solution containing 0.5 mol/liter of n-heptane, 0.1 mol/liter of cobaltic acetate, 0.2 mol/liter of sulphuric acid, and 1.5 mol/liter of trichlorobromomethane in acetic acid was kept at 20°C, without stirring, in the dark, and under a nitrogen atmosphere at atmospheric pressure. After 18 hours the reaction mixture was treated and analyzed as in Example I.. It was thus determined that 10% of the n-heptane employed had been converted to yield the following products:

heptyl bromides:100% (isomer 1: 4%; 2: 47%; 3: 33%; 4: 16%)

EXAMPLE XVII

This example illustrates the bromination of n-heptane by means of the system comprising cobaltic acetate, sulphuric acid and bromine.

Example XVI was repeated, rpelacing trichlorobromomethane with bromine at the concentration of 0.15 mol/liter. After 20 minutes the reaction mixture was treated and analyzed as in Example I. It was found that 6% of the n-heptane had been converted to yield the following products:

heptyl bromides:100% (isomer 1: 1%; 2: 51%; 3.32%; 4: 16%)

This example shows the possibility of employing molecular bromine as a bromination agent.

EXAMPLE XVIII

This example illustrates the bromination of n-heptane by means of the system comprising cobaltic acetate, trichloroacetic acid, and trichlorobromomethane.

A solution containing 0.5 mol/liter of n-heptane, 0.1 mol/liter of cobaltic acetate, 1.5 mol/liter of trichloroacetic acid, and 1.5 mol/liter of trichlorobromomethane in acetic acid was kept at 20°C, without stirring, in the dark, and under a nitrogen atmosphere at atmospheric pressure. After 24 hours the reaction mixture was treated and analyzed as in Example I. It was found that 8% of the n-heptane employed had been converted to yield the following products:

heptyl bromides:100% (isomer 1: 5%; 2: 66%; 3: 20%; 4: 9%)

This example shows that in the presence of a bromine donor, trichloroacetic acid solely operates as an activator and not as a halogen donor.

EXAMPLE XIX

This example illustrates the bromination of n-heptane by means of the system comprising cobaltic acetate, trichloroacetic acid and bromine.

Example XVII was repeated, replacing sulphuric acid with trichloroacetic acid at the concentration of 1.5 mol/liter. Analysis showed that after 4 hours of reaction, 3.6% of the n-heptane employed had been converted to yield the following products:

heptyl bromides:100% (isomer 1: 2%; 2: 60%; 3: 24%; 4: 14%)

EXAMPLE XX

This example illustrates the bromination of n-heptane by means of the system comprising cobaltic acetate and tribromoacetic acid.

A solution containing 0.5 mol/liter of n-heptane, 0.1 mol/liter of cobaltic acetate, and 1.5 mol/liter of tribromoacetic acid in acetic acid was kept at 20°C, without stirring, in the dark, and under a nitrogen atmosphere at atmospheric pressure. After 19 hours the reaction mixture was treated and analyzed as in Example I. It was thus determined that 6.1% of the n-heptane employed had been converted to yield the following products:

heptyl bromides:100% (isomer 1: 1%; 2: 57%; 3: 27%; 4: 15%)

It is plain that like trichloroacetic acid in Example IX, tribromoacetic acid can simultaneously operate as an activator and as a halogen donor.

EXAMPLE XXI

This example illustrates the bromination of n-heptane by means of the system comprising cobaltic acetate and dibromoacetic acid.

Example XX was repeated, replacing tribromoacetic acid with dibromoacetic acid in the same concentration. Analysis established that 2.3% of the n-heptane employed had been converted to yield the following products:

heptyl bromides:100% (isomer 1: 1%; 2: 62%; 3: 24%; 4: 13%)

EXAMPLE XXII

This example illustrates the bromination of n-heptane by means of a system comprising cobaltic acetate, trifluoroacetic acid and monobromoacetic acid.

Example XX was repeated, replacing tribromoacetic acid with trifluoroacetic acid and monobromoacetic acid, each at a concentration of 1.5 mol/liter. Analysis showed that 2.5% of the n-heptane employed had been converted to yield the following products whose relative proportions are given as molar percentages:

heptyl bromides:84% (isomer 1: 2%; 2: 60%; 3: 26%; 4: 12%)
heptyl acetates:8% (isomer 1: 0%; 2: 68%; 3: 22%; 4: 10%)
heptanones:6% (isomer   2: 75%; 3: 17%; 4: 8%)
heptanols:2% (isomer 1: 0%; 2: 70%; 3: 20%; 4: 10%)

The same products are obtained if trifluoroacetic acid is not added to the system, but they correspond to no more than a conversion of 0.6% of the n-heptane employed.

This example shows that monobromoacetic acid can be employed in the present invention as a halogen donor, but that its acidity is insufficient for effectively performing the function of an activator.

EXAMPLE XXIII

This example illustrates the bromination of n-heptane by means of the sytem comprising cobaltic acetate, trifluoroacetic acid, and alpha-bromoisobutyric acid.

Example XX was repeated, replacing tribromoacetic acid with trifluoroacetic acid and alpha-bromoisobutyric acid, each at the concentration of 1.5 mol/liter. Analysis showed that 2.2% of the n-heptane employed had been coverted to yield the following products whose relative proportions are given as molar percentages:

heptyl bromides:91% (isomer 1: 3%; 2: 75%; 3: 16%; 4: 6%)
heptanones:5% (isomer   2: 85%; 3: 10%; 4: 5%)
heptyl acetates: 3% (isomer 1: 0%; 2: 79%; 3: 15%; 4: 6%)
heptanols:1% (only isomer 2 was detectable)

The same products are obtained if trifluoroacetic acid is not added to the system, but they correspond to only 0.4% of the n-heptane employed.

This example shows that like monobromoacetic acid, alpha-bromoisobutyric acid can operate as a halogen donor but not as an activator.

EXAMPLE XXIV

This example illustrates the chlorination of n-decane by means of the system comprising cobaltic acetate and trichloroacetic acid.

A solution containing 0.5 mol/liter of n-decane, 0.1 mol/liter of cobaltic acetate, and 1.5 mol/liter of trichloroacetic acid in acetic acid was kept at 20°C, without stirring, under a nitrogen atmosphere at atmospheric pressure. After 18 hours the reaction mixture was treated and analyzed as in Example I. It was thus determined that approximately 63 percent of the products obtained consisted of decyl chlorides (isomer 1: 5%; 2: 67%; 3: 13%; 4 + 5: 15%).

EXAMPLE XXV

This example illustrates the chlorination of 2-methylpentane by means of the system comprising cobaltic acetate and trichloroacetic acid.

A solution containing 0.8 mol/liter of 2-methylpentane, 0.2 mol/liter of cobaltic acetate, and 1.5 mol/liter of trichloroacetic acid in acetic acid was kept at 20°C, without stirring, under a nitrogen atmosphere at atmospheric pressure. After 30 hours the reaction mixture was treated and analyzed as in Example I. Analysis enabled to identify the following products whose relative proportions are given as molar percentages:

2-methylchloropentanes:50 %(isomer 1: 6%; 2: 5%; 3: 2%; 4: 74%; 5: 13%)
2-methylpentanol acetates:44 %(isomer 1: 0%; 2: 66%; 3: 2% 4: 32%; 5: 0%)
2-methylpentanols:4 %(isomer 1: 0%; 2: 35%; 3: 34% 4: 30%; 5: 0%)

2-methylpentanones:2% (only isomer 4 was detectable)

It is obvious that despite the presence of a tertiary hydrogen atom, the chlorination of the hydrocarbon occurs principally on the methylene group situated in the 4 position.

EXAMPLE XXVI

This example illustrates the chlorination of 2-methylhexane by means of the system comprising cobaltic acetate and trichloroacetic acid.

A solution containing 0.5 mol/liter of 2-methylhexane, 0.1 mol of cobaltic acetate, and 1.5 mol/liter of trichloroacetic acid in acetic acid was kept at 20°C, without stirring, under a nitrogen atmosphere at atmospheric pressure. After 24 hours the reaction mixture was treated and analyzed as in Example I. The analysis enabled to identify the following products whose relative proportions are given as molar percentages:

2-methylchlorohexanes: 59% (isomer 1: 55; 2 + 3 + 4: 16%; 5: 74%; 6 5%)
2-methylhexanol acetates:27% (isomer 1: 0%; 2: 73%; 3: 0%; 4: 0%; 5: 27%; 6: 0%)
2-methylhexanols:8% (isomer 1: 0%; 2: 38%; 3: 9%; 4: 9%; 5: 44%; 6: 0%)
2-methylhexanones:6% (only isomer 5 was detectable)

EXAMPLE XXVII

Following the procedure of Example XXVI but using a medium as anhydrous as possible, the following products were obtained, whose relative proportions are given as molar percentages:

2-methylchlorohexanes:71% (isomer 1: 4%; 2 + 3 + 4: 16%, 5: 75%; 6: 5%)
2-methylhexanol acetates:21% (isomer 1: 0%; 2: 81%; 3: 0%; 4: 0%; 5: 19%; 6: 0%)
2-methylhexanols:5% (isomer 1: 0%; 2: 41%; 3: 0%; 4: 7%; 5: 52%; 6: 0%)
2-methylhexanones:3% (only isomer 5 was detectable)

This example confirms that it is of interest to operate in an anhydrous medium to promote the formation of halides.

What is claimed is:

1. The process for selective halogenation of a straight-chain or branched-chain hydrocarbon of the type $CH_3$ —$CH_2$ —R in which R is a primary alkyl group, to preferentially halogenate the carbon atom of a methylene group in alpha-position to a terminal methyl group, comprising reacting said hydrocarbon in the liquid phase with a halogen donor selected from the group consisting of molecular bromine and the halogen compounds having the formula

wherein X is a chloro or bromo radical; $Y_1$ and $Y_2$ are members of the group consisting of the fluoro, chloro, bromo, cyano, carboxyl, alkoxycarbonyl, hydrogen and hydrocarbon radicals; $Y_3$ is a fluoro, chloro, bromo, cyano, carboxyl, or alkoxycarbonyl radical; in the presence of a cationic cobaltic salt of a lower fatty acid and an activator selected from the group consisting of sulphuric acid, perchloric acid, trifluoroacetic acid, trichloroacetic acid, tribromoacetic acid, dichloroacetic acid, dibromoacetic acid, boron trifluoride and mixtures thereof, at a temperature between −20°C and +100°C, and in the absence of molecular oxygen.

2. The process as defined in claim 1 wherein the radical R comprises comprises more than 2 carbon atoms.

3. The process as defined in claim 1 wherein the halogen donor is a halomethane comprising at least two halogen atoms selected from the group consisting of chlorine and bromine.

4. The process as defined in claim 1 wherein the halogen donor is a compound comprising at least two chlorine atoms linked to a carbon atom in alpha position to a radical selected from the group consisting of carbonyl and cyano.

5. The process as defined in claim 4 wherein the halogen donor is trichloroacetic acid.

6. The process as defined in claim 1 wherein the halogen donor is a compound comprising at least one bromine atom linked to a carbon atom in alpha-position to a radical selected from the group consisting of carbonyl and cyano.

7. The process as defined in claim 6 wherein the halogen donor is tribromoacetic acid.

8. The process as defined in claim 1 wherein the cobaltic salt is the salt of a fatty acid comprising from 2 to 4 carbon atoms.

9. The process as defined in claim 8 wherein the cobaltic salt is cobaltic acetate.

10. The process as defined in claim 1 wherein the reaction is performed in the presence of a solvent selected from the group consisting of the fatty acids having 2 to 4 carbon atoms and the methyl and t-butyl esters of said fatty acids.

11. The process as defined in claim 10 wherein the solvent is acetic acid.

12. The process as defined in claim 1 wherein the reaction is performed in an anhydrous medium.

* * * * *